United States Patent
Ogawa

(10) Patent No.: US 9,339,417 B2
(45) Date of Patent: May 17, 2016

(54) ROLL TAPE

(71) Applicant: Makiko Ogawa, Hyogo (JP)

(72) Inventor: Makiko Ogawa, Hyogo (JP)

(*) Notice: Subject to any disclaimer, the term of this patent is extended or adjusted under 35 U.S.C. 154(b) by 28 days.

(21) Appl. No.: 14/374,441

(22) PCT Filed: Jan. 22, 2013

(86) PCT No.: PCT/JP2013/051197
§ 371 (c)(1),
(2) Date: Jul. 24, 2014

(87) PCT Pub. No.: WO2013/111750
PCT Pub. Date: Aug. 1, 2013

(65) Prior Publication Data
US 2014/0363605 A1 Dec. 11, 2014

(30) Foreign Application Priority Data

Jan. 27, 2012 (JP) .................. 2012-015709

(51) Int. Cl.
| | | |
|---|---|---|
| C09J 7/02 | (2006.01) |
| A61F 13/02 | (2006.01) |
| A61F 15/00 | (2006.01) |
| C09J 7/04 | (2006.01) |
| A61F 13/00 | (2006.01) |

(52) U.S. Cl.
CPC ........... *A61F 13/0269* (2013.01); *A61F 15/006* (2013.01); *C09J 7/04* (2013.01); *A61F 2013/00795* (2013.01); *A61F 2013/00812* (2013.01); *A61F 2013/00842* (2013.01); *C09J 2201/20* (2013.01); *C09J 2400/263* (2013.01); *Y10T 428/15* (2015.01)

(58) Field of Classification Search
CPC .................. C09J 2201/20; A61F 2013/00812
USPC .......................................... 428/43
See application file for complete search history.

(56) References Cited

U.S. PATENT DOCUMENTS

2012/0177860 A1   7/2012   Numazu et al.

FOREIGN PATENT DOCUMENTS

| JP | 2-092889 U | 7/1990 |
| JP | 6-047071 | 2/1994 |
| JP | 7-101603 | 4/1995 |
| JP | 8-239634 | 9/1996 |
| JP | 9-502111 | 3/1997 |
| JP | 2000-116695 | 4/2000 |
| JP | 3086908 U | 4/2002 |
| JP | 2003-285968 | 10/2003 |
| JP | 2006-006514 | 1/2006 |
| JP | 2006-320471 | 11/2006 |
| KR | 20090002386 | 1/2009 |
| WO | 95/06450 | 3/1995 |
| WO | 2011/121659 | 10/2011 |

OTHER PUBLICATIONS

Extended European Search Report issued in corresponding European Application No. 13741654.1, Aug. 31, 2015, 4 pages.

*Primary Examiner* — Alexander Thomas
(74) *Attorney, Agent, or Firm* — Hamre, Schumann, Mueller & Larson, P.C.

(57) ABSTRACT

A long cut line 21 extending along a virtual cutting line D is arranged in a central region A of an adhesive tape 1. The length of the long cut line 21 is made longer than a length of a second adjacent cut line 22 arranged in an adjacent region B and an outer cut line 23 arranged in an outer region C. The adjacent region B and the outer region C of the adhesive tape 1 have a tensile strength that can withstand the tensile stress generated when the adhesive tape 1 is fed out.

5 Claims, 15 Drawing Sheets

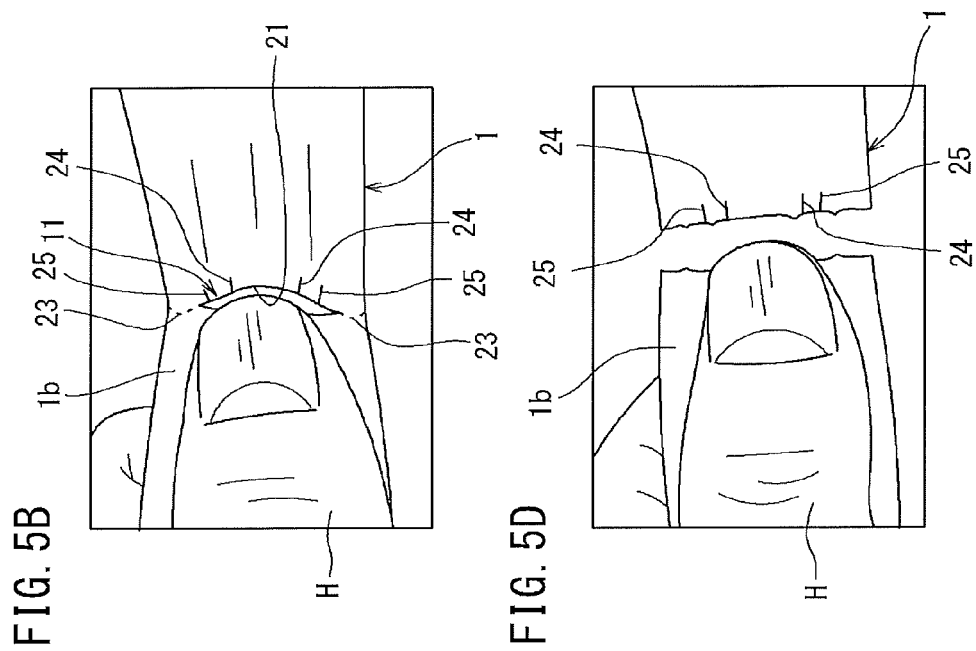
FIG. 5A
FIG. 5B
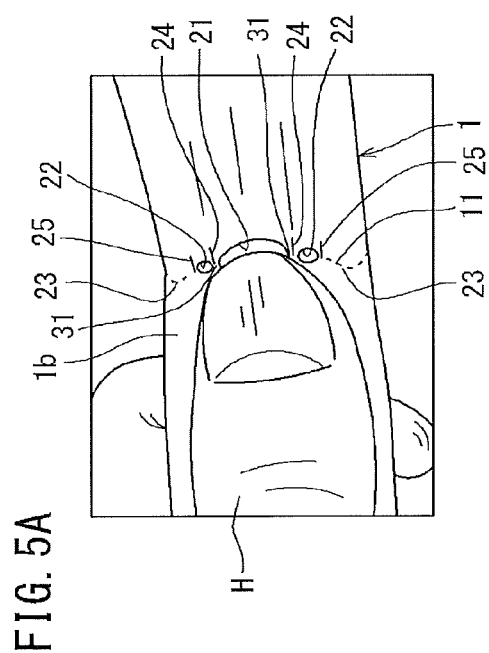
FIG. 5C
FIG. 5D

ROLL TAPE

TECHNICAL FIELD

The present invention relates to a roll tape in which a long adhesive tape is wound.

BACKGROUND ART

At medical fronts, an adhesive tape in which an adhesive is stacked on an adhesive tape main body such as a surgical tape, adhesive plaster, and the like has been heavily used from the prior art. Such adhesive tape is normally provided as a roll tape wound around a cylindrical roll core. The adhesive tape is often attached directly to the skin of the human body, and thus air permeability, flexibility, and moisture permeability are demanded. The adhesive tape in which the adhesive tape main body is formed with a thin non-woven cloth made of rayon fiber, and the like has been provided (see e.g., Patent Literature 1).

CITATION LIST

Patent Literature

Patent Literature 1: Japanese Unexamined Patent Publication No. 2000-116695

SUMMARY OF INVENTION

Technical Problem

The adhesive tape in which the adhesive tape main body is formed with a thin non-woven cloth excels in air permeability, flexibility, moisture flexibility, and the like and is less likely to be felt uncomfortable when attached to the skin, and also has a function suited for the adhesive tape. However, the non-woven cloth, in particular has a strong tensile strength, and thus cannot be easily cut even when attempting to pull and cut the adhesive tape with fingertips, for example. Furthermore, when attempting to forcibly cut the adhesive tape, the outer appearance of the cut edge may be impaired such as that the cut edge may not be perpendicular to a longitudinal direction of the adhesive tape, or the cut edge may be in a zigzag-shape.

The adhesive tape is thus normally cut without impairing the outer appearance of the cut edge by using a pair of scissors.

However, when cutting the adhesive tape with scissors, additional operations such as preparing the scissors, holding and placing the scissors, and the like are required compared to when cutting the adhesive tape with hand. Thus, the additional operation as described above increases as the area to be attached with the adhesive tape increases, and hence there is a great waste in time and effort.

In order to efficiently cut with scissors, the cutting operation of the adhesive tape may be carried out collectively, and a cut strip of the adhesive tape having the necessary length may be prepared in plural in advance. In this case, however, the length might not be appropriate or the number exceeding the required number of cut strips might be cut when the adhesive tape is actually attached to the human body, which may lead to wasteful use of the adhesive tape.

Furthermore, when fixing gauze placed on the face, and the like of a patient with the adhesive tape and cutting such adhesive tape with scissors at the medical front, the scissors is used close to the face of the patient, which may give a great sense of discomfort to the patient.

Thus, consideration is made to form in advance a cut line X in a perforation form along a width direction of the adhesive tape T, as shown in FIG. 14A, so that the adhesive tape can be cut with the fingers of the hand without impairing the outer appearance of the cut edge.

However, if the length of the cut line X is made long or the length of a uncut portion Y, which is between the cut line X and the cut line X, is made small so that the adhesive tape T can be easily cut, the tensile strength of the adhesive tape becomes weak at the portion formed with the cut line X. Thus, if the adhesive tape T is pulled in the longitudinal direction while being torn off from the roll, the adhesive tape T may be easily cut with one side edge T1 in the width direction as a starting point or with the entire width direction instantly torn, as shown in FIG. 14B. The adhesive tape T thus might be cut at the cut line portion of an unwilling position other than the position desired to be cut by simply pulling a distal end of the adhesive tape T in the longitudinal direction to feed out the adhesive tape from the roll tape.

In order to prevent the adhesive tape from being easily cut at the unwilling position, consideration is made to thicken the thickness of the nonwoven cloth itself and increase the tensile strength of the portion formed with the cut line X. However, thickening the thickness of the nonwoven cloth affects the flexibility, thus increasing the uncomfortable feeling when the adhesive is attached to the skin.

Further, as shown in FIGS. 15A and 15B, the tensile strength of the adhesive tape can be increased by making the length of the uncut portion Y relatively long with respect to the length of the cut line X, but in such a case, the function for the cut line X lowers. Thus, when attempting to cut the adhesive tape T in a pulled state, the adhesive tape T cannot be cut unless pulled with a very strong force, and the outer appearance of the cut edge of the uncut portion Y, in particular, is impaired if forcibly pulled and cut.

For the above reasons, a measure for easily cutting the adhesive tape with fingertips without impairing the outer appearance of the cut edge and without using scissors when cutting the adhesive tape made of thin nonwoven cloth, and the like is desired.

In light of the foregoing, it is an object of the present invention to provide a roll tape in which the adhesive tape can be easily cut at a desired position with fingertips without impairing the outer appearance of the cut edge.

Solution to Problem (1) The present invention relates to a roll tape in which a cut line is formed in plural along a virtual cutting line extending in a width direction of an adhesive tape, the cut line being arranged to cut an adhesive tape in a roll form to a desired length while being fed out by a predetermined length, the adhesive tape having an adhesive stacked on one surface of a long tape main body, wherein the cut line includes a long cut line, which is arranged in a central region in a width direction of a virtual cutting line and is opened by feeding out the adhesive tape, and which cuts the adhesive tape along the cut line arranged in the regions of both sides in a width direction of the central region with both ends of the central region as starting points by pressing the central region or the vicinity with a finger in the opened state, the long cut line being longer than the cut line arranged in the regions of both sides, and the regions of both sides having a tensile strength that withstands a tensile stress generated when the adhesive tape is fed out.

According to the roll tape of the configuration described above, the long cut line longer than the cut line arranged in the regions of both sides is configured in the central region in the width direction of the virtual cutting line in the adhesive tape, and thus when gripping the roll tape with one hand and pulling the distal end of the adhesive tape with the other hand to feed out the wound adhesive tape while tearing from the roll portion, the long cut line greatly opens in the longitudinal direction of the tape than the cut line of the regions of both sides.

The adhesive tape thus tends to be broken toward the outer side in the width direction of the tape with both ends of the long cut line as the starting points. However, since the regions of both sides on both sides of the central region have the tensile strength that can withstand the tensile stress generated when feeding out the adhesive tape, the adhesive tape can be inhibited from being cut by the regions of both sides of the central region.

When the operator presses the long cut line portion or the vicinity thereof at the position desired to be cut in the adhesive tape with the fingertip (tip of the nail) of one hand which is gripping the roll tape while pulling the adhesive tape with the other hand in this state, stress concentration occurs in the central region of the adhesive tape, thus tearing and widening both ends of the long cut line. The region on both sides of the long cut line thus can be cut along the virtual cutting line.

(2) In the roll tape described above, the cut line preferably includes a first adjacent cut line arranged in an adjacent region adjacent on both sides of the central region of the regions of both sides, the first adjacent cut line extending in a longitudinal direction of the adhesive tape while intersecting with the virtual cutting line.

In this case, the tensile strength of the adjacent region can be easily ensured since the first adjacent cut line extends in the longitudinal direction of the adhesive tape. Thus, the tensile strength of the regions of both sides can be easily ensured by the adjacent region for the adhesive tape having a thin thickness. Moreover, the adjacent region can be easily cut since the first adjacent cut line intersects with the virtual cutting line.

(3) In the roll tape described above, the cut line preferably includes an outer cut line arranged in plural in a perforation form in an outer region from an end in the width direction of the adjacent region of the regions of both sides to a side edge of the adhesive tape.

In this case, when both ends of the long cut line are torn and widened and the adjacent region is cut, the region up to the outer region can be easily cut without impairing the outer appearance by the outer cut line arrayed in plural in the outer region.

(4) A second adjacent cut line extending along the virtual cutting line may be arranged adjacent to the first adjacent cut line in the adjacent region.

In this case, the roll tape having a wide width can also be easily cut without impairing the outer appearance by the second adjacent cut line.

(5) The tape main body is preferably made from a nonwoven cloth. In this case, the tape main body made of nonwoven cloth that is difficult to cut with hand, can also be easily cut without impairing the outer appearance.

Advantageous Effects of Invention

According to the roll tape of the present invention, the adhesive tape can be easily cut at an arbitrary position with the fingertip without impairing the outer appearance of the cut edge.

BRIEF DESCRIPTION OF DRAWINGS

FIG. 5 is a plan view showing the procedure for cutting the adhesive tape.

FIG. 5A is a plan view showing a state in which the long cut line is pressed with the fingertip of the thumb.

FIG. 5B is a plan view showing a state in which the long cut line is broken and pushed open in the longitudinal direction.

FIG. 5C is a plan view showing a state in which the cutting of the outer region is advanced along the plurality of outer cut lines.

FIG. 5D is a plan view showing a state in which the adhesive tape is cut.

DESCRIPTION OF EMBODIMENTS

Embodiments of the present invention will be hereinafter described based on the accompanying drawings.

Figure 1:
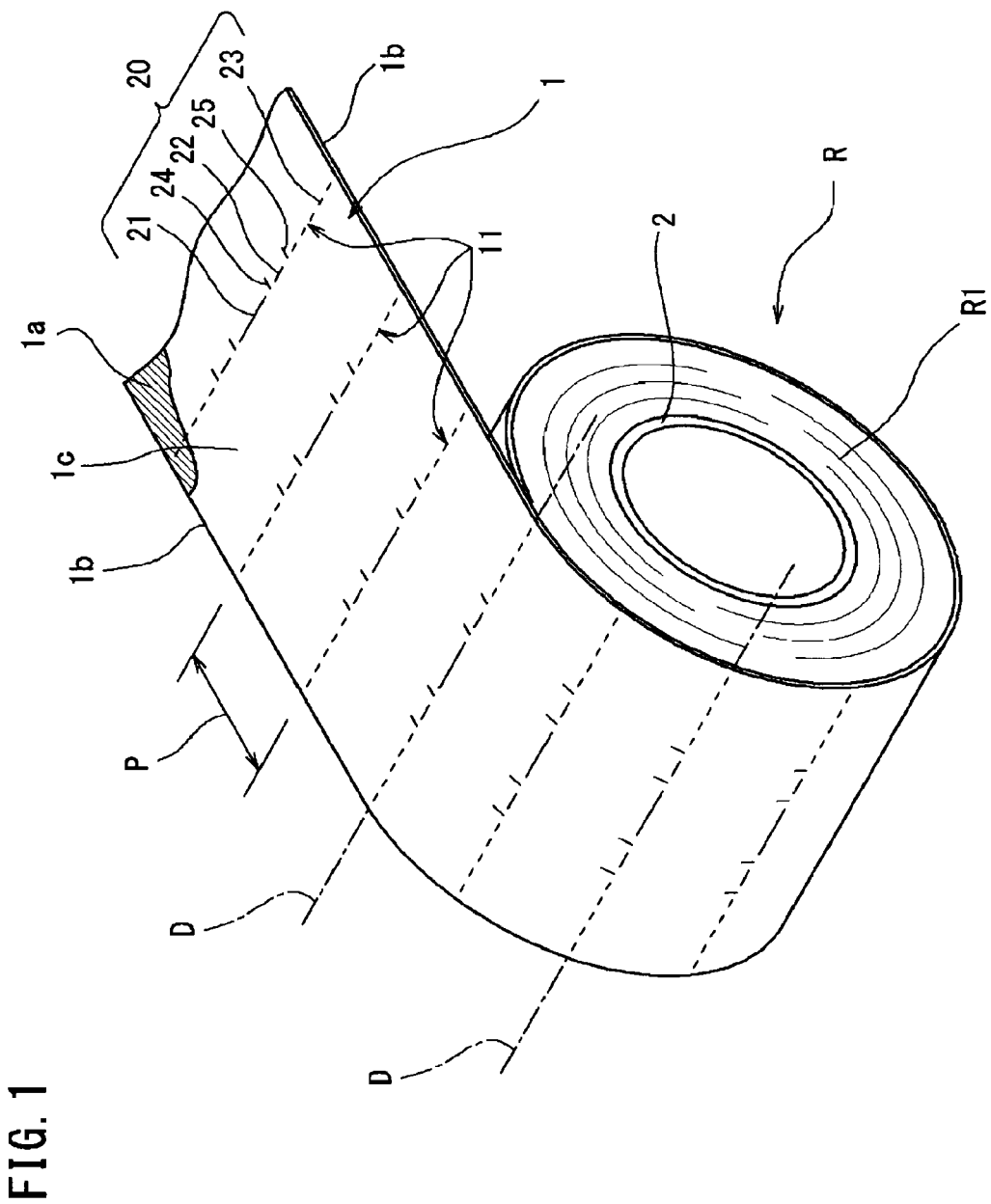
FIG. 1 is a perspective view of a roll tape according to a first embodiment of the present invention.

FIG. 1 is a perspective view showing a roll tape R according to a first embodiment of the present invention. The roll tape R is obtained by multiply winding a long adhesive tape 1 around a cylindrical roll core 2, and is used as a surgical tape. The surgical tape is used to fix bandages, gauzes, and the like in the medical field, and can be directly attached to the skin, and the like of the patient.

A tape main body 1c of the adhesive tape 1 is made from a very thin nonwoven cloth using rayon fiber, and the like, and has high air permeability, flexibility, and moisture permeability. On a back surface of the adhesive tape 1, an adhesive 1a for attaching the adhesive tape 1 to an attaching portion such as the skin, and the like of the patient is stacked.

A great number of cutting portions 11 for selectively cutting the adhesive tape 1 along the width direction is formed in the adhesive tape 1. The cutting portions 11 are formed at every constant interval along a longitudinal direction of the adhesive tape 1 (hereinafter simply referred to as "longitudinal direction"). A cut line 20 of a plurality of types is formed in the cutting portion 11 along a virtual cutting line D linearly extending in the width direction. The cutting portion 11 is formed at a pitch P of 10 mm along the longitudinal direction.

Figure 2:
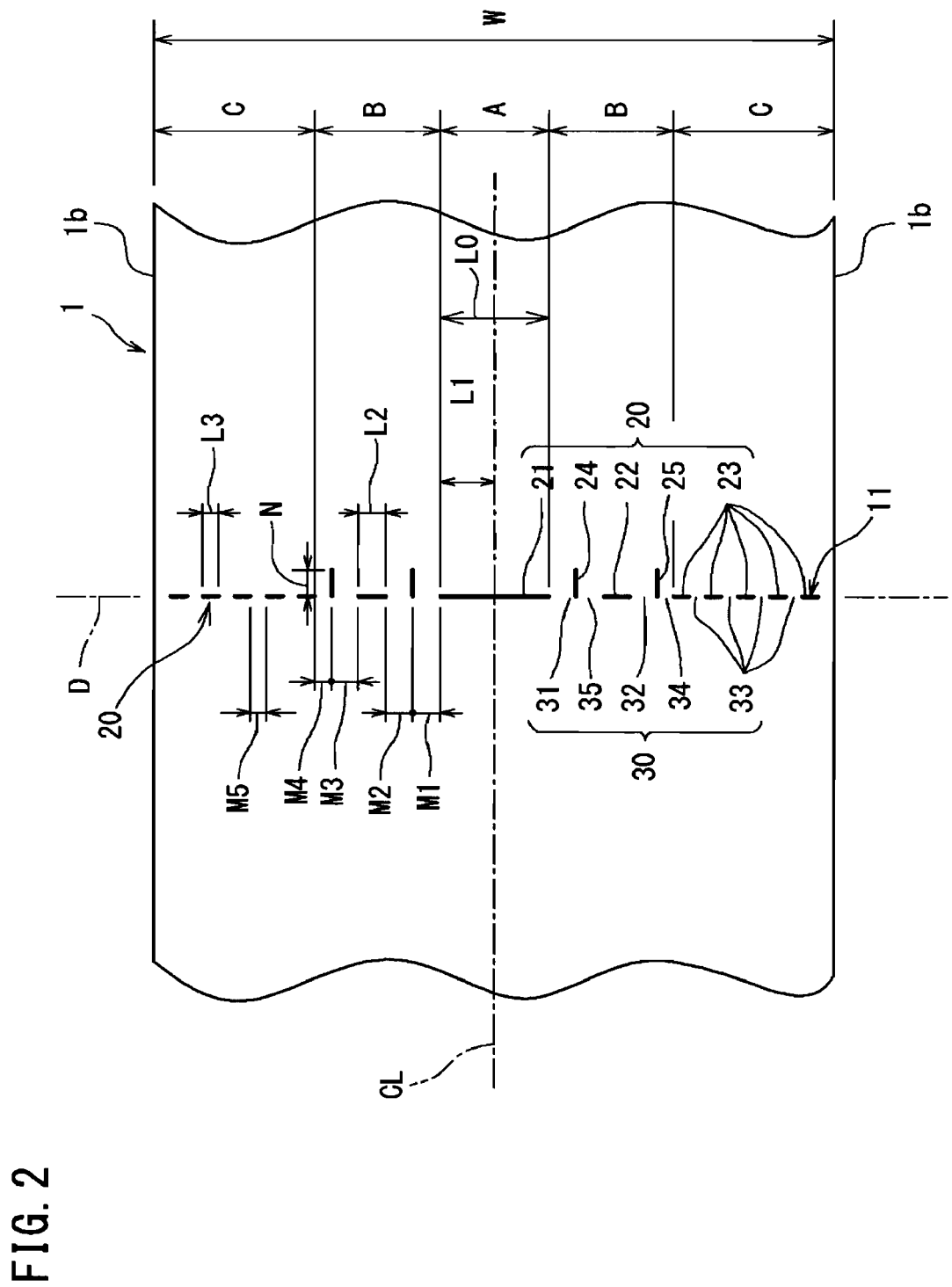
FIG. 2 is a partially enlarged view showing a cutting portion of an adhesive tape.

With also reference to FIG. 2, in the cutting portion 11, the virtual cutting line D of the adhesive tape 1 is sectionalized to a central region A set at a central part in the width direction of the adhesive tape 1 (hereinafter simply referred to as "width direction"), an adjacent region B set adjacent on both sides in the width direction of the central region A, and an outer region C set in a range from both ends in the width direction of the adjacent region B to a side edge b of the adhesive tape 1.

Each of cut lines 20 arranged in the cutting portion 11 is passed through the adhesive tape 1, and a portion between the cut lines 20 adjacent to each other configures an uncut portion 30 in which the cut line is not provided. The cut line 20 on one side in the width direction and the cut line 20 on the other side in the width direction are formed to be line symmetric with respect to a center line CL of the adhesive tape 1.

Each of the cut lines 20 includes a long cut line 21 arranged in the central region A of the adhesive tape 1, a pair of first adjacent cut lines 24, 25 and a second adjacent cut line 22 arranged in the adjacent region B, and an outer cut line 23 arranged in the outer region C.

The long cut line 21 is arranged over the entire width of the central region A along the virtual cutting line D.

The first adjacent cut lines 24, 25 are respectively extended in the longitudinal direction with the virtual cutting line D as a base end. One first adjacent cut line 24 is adjacent to the end of the long cut line 21 by way of the uncut portion 31, and the other first adjacent cut line 25 is adjacent to the outer cut line 23 closest to the adjacent region B by way of an uncut portion 34. The first adjacent cut lines 24, 25 merely need to intersect with the virtual cutting line D, respectively, and do not necessarily need to have the virtual cutting line D as the base end.

The second adjacent cut line 22 is extended along the virtual cutting line D, and is arranged adjacent to the first adjacent cut lines 24, 25 by way of uncut portions 32, 35.

Regions of both sides configured by the adjacent region B and the outer region C positioned in the width direction of the central region A have the tensile strength that can withstand the tensile stress generated when feeding out the adhesive tape 1 from a roll portion R1. The tensile strength is ensured by setting the uncut portions 31, 32, 34, 35 of the adjacent region B to greater than or equal to a predetermined value. Since the first adjacent cut lines 24, 25 are extended in the longitudinal direction and not the width direction, the tensile strength in the longitudinal direction in the adjacent region B is practically not lowered. Thus, the tensile strength of the adjacent region B can be easily ensured even with a tape main body 1c having a thin thickness.

An entire width L0 (width direction dimension L1×2 on one side) of the long cut line 21, a width direction dimension L2 of the second adjacent cut line 22, and a width direction dimension L3 of the outer cut line 23 are set to satisfy the following relationship.

$$L0 > L2 > L3$$

Therefore, the dimension in the longitudinal direction of an opening that is formed in the adhesive tape 1 when the adhesive tape 1 is pulled in the longitudinal direction becomes large in the order of the outer cut line 23, the second adjacent cut line 22, and the long cut line 21, as described below.

$$\text{Outer cut line 23} < \text{second adjacent cut line 22} < \text{long cut line 21}$$

Further, the entire width L0 of the long cut line 21 is, for example, set to 1.5 times to six times the width direction dimension L2 of the second adjacent cut line 22 and the width direction dimension L3 of the outer cut line 23, and more preferably set to three times to five times the width direction dimension L2 of the second adjacent cut line 22 and/or six times to seven times the width direction dimension L3 of the outer cut line 23. Each of such dimensions is appropriately set in view of the material, the width direction dimension, and the thickness of the adhesive tape 1.

As will be descried later, the long cut line 21 is opened by feeding out the adhesive tape 1, and the operator specifies the cut line 20 to cut with the opened long cut line 21.

Therefore, the entire width L0 of the long cut line 21 is set to a value that can be opened to an extent visually recognizable by the operator when the adhesive tape 1 is fed. Although depending on the material and the thickness of the adhesive tape 1, if the width L0 is set to greater than or equal to 2 mm as a specific value, the opening of the long cut line 21 when the adhesive tape 1 is fed out can be easily visually recognized.

Furthermore, as will be described later, when the adhesive tape 1 is pressed with a finger, both ends of the long cut line 21 become the starting points at the time of cutting the adhesive tape 1. Thus, the entire width L0 of the long cut line 21 is set to a dimension in which a sufficient stress can be acted to an extent that both ends of the long cut line 21 can be ripped open when the adhesive tape 1 is pressed with a finger. For example, if the entire width L0 is smaller than or equal to the width dimension of the finger of a typical adult, more preferably, smaller than or equal a width dimension of a nail, the stress generated by pressing down the finger or the nail can be acted over the entire width direction of the long cut line 21. Thus, it is preferable that the entire width L0 is smaller than or equal to the width dimension of the finger of the typical adult, and more preferably, smaller than or equal to the width dimension of the nail.

The entire width L0 of the long cut line 21 is preferably set to be smaller than or equal to ⅓ of the width dimension W of the adhesive tape 1. This is because, although depending on the material and the width dimension W of the adhesive tape 1, the tensile strength that can withstand the tensile stress generated when feeding out the adhesive tape 1 may not be maintained if the regions of both sides are generally smaller than or equal to ⅓ of the width dimension W.

The necessity to open the second adjacent cut line 22 and the outer cut line 23 when the adhesive tape 1 is fed out is low. Thus, the width dimensions L2, L3 of the second adjacent cut line 22 and the outer cut line 23 are set to values smaller than the entire width L0 of the long cut line 21 so that the opening when the adhesive tape 1 is fed out becomes smaller than the long cut line 21 or the opening barely is formed to further emphasize the opening of the long cut line 21.

Such width dimensions L2, L3 of the second adjacent cut line 22 and the outer cut line 23 are preferably defined according to the conditions described above.

In the present embodiment, the width direction dimension W of the adhesive tape 1, the width direction dimensions L1 to L3 of each of the cut lines 20, the width direction dimensions M1 to M5 of each uncut portion, and a longitudinal direction dimension N of the first adjacent cut lines 24, 25 are set as below.

W=25 mm
L1=2 mm
L2=1 mm
L3=0.59 mm
M1=1 mm
M2=1 mm
M3=1 mm
M4=0.59 mm
M5=0.59 mm
N=1 mm

Next, a procedure when the operator cuts the roll tape R having the configuration described above will now be described.

Figure 3:
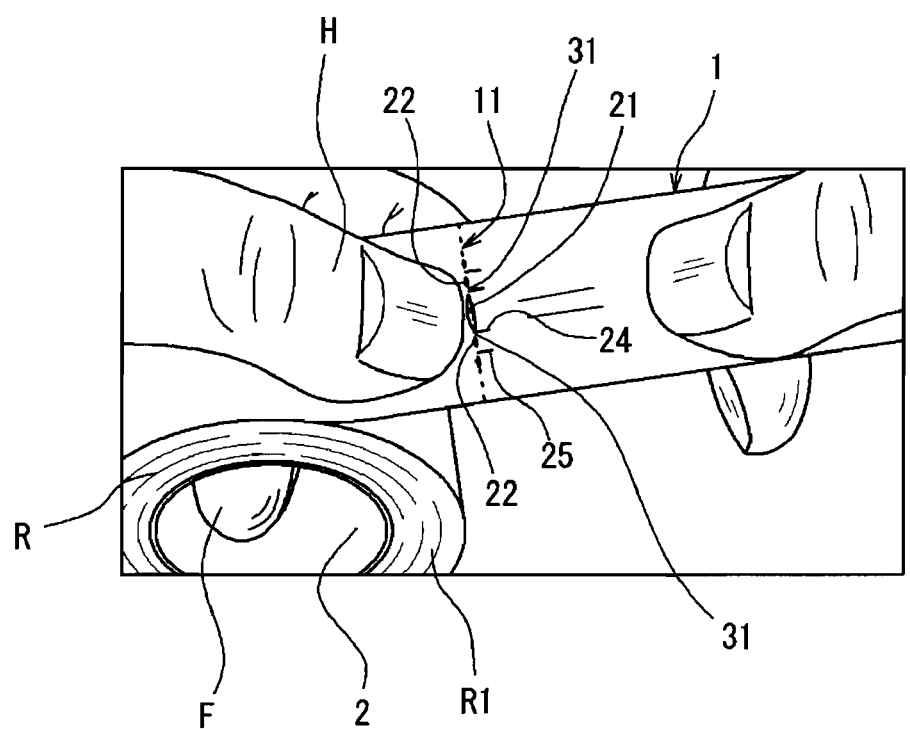
FIG. 3 is a perspective view showing a state in which the adhesive tape is fed out from a roll portion.

As shown in FIG. 3, the operator first grips the roll R1 portion of the roll tape R with one hand, and grabs the free end side of the adhesive tape 1 with the other hand. In this case, the roll tape R is preferably gripped with a forefinger F (or middle finger, or middle finger and ring finger) inserted to the roll core 2 and a thumb H placed along the outer circumference of the roll R1.

Then, the adhesive tape 1 is pulled in the longitudinal direction and fed out by a necessary length while being torn off from the roll R1. Thus, when the adhesive tape 1 is pulled in the longitudinal direction, the long cut line 21 opens greatly in the longitudinal direction than the other cut lines, as shown in FIG. 3. In this case, the adhesive tape 1 is broken toward the outer side in the width direction with both ends of the long cut line 21 as the starting points. However, since the adjacent region B and the outer region C have, as a whole, the tensile strength that can withstand the tensile stress generated when feeding out the adhesive tape 1 as regions of both sides described above, the adhesive tape 1 can be inhibited from being cut by the regions of both sides (adjacent region B and outer region C).

The long cut line 21 is greatly opened in this state, and hence the operator can easily specify the cut line 20 to cut. The fingertip (tip of the nail) of the thumb H of one hand gripping the roll R1 is then pressed on the long cut line 21 portion of the specified cut line 20 while a state of pulling the adhesive tape 1 is maintained (see FIG. 5A). The operation of pressing the fingertip on the long cut line 21 portion can be easily carried out by pivoting the roll R1 by a constant angle in the clockwise direction in FIG. 4A, and gradually winding the adhesive tape 1 around a ball H1 of the fingertip. In this case, the center position in the width direction of the fingertip and the center position in the width direction of the long cut line 21 are substantially coincided.

Figure 4A:
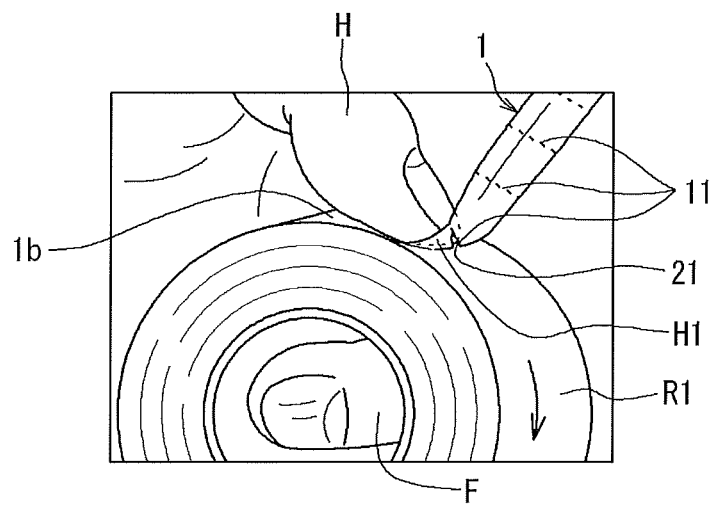
FIG. 4A is a perspective view showing a state in which the adhesive tape is wound around a ball of a fingertip.
Figure 4B:
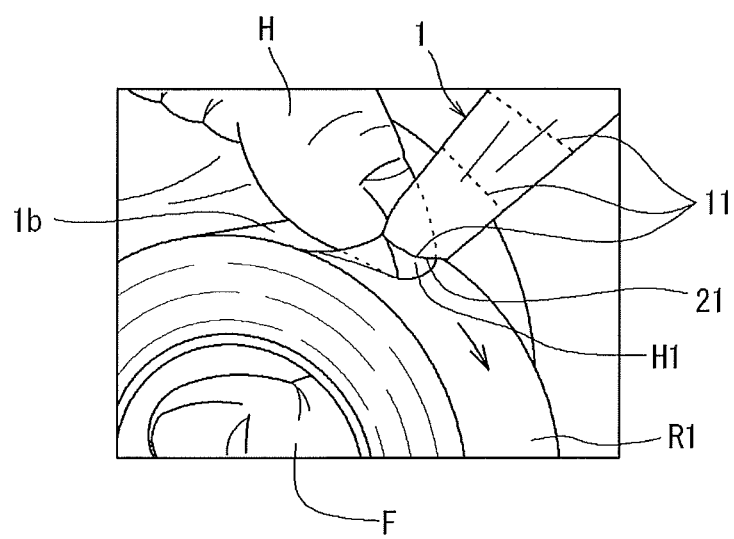
FIG. 4B is a perspective view showing which the long cut line is broken and pushed open in the longitudinal direction.

Thus, when the adhesive tape 1 is pressed with the thumb H, the tensile stress of the central region A of the adhesive tape 1 increases and the stress concentration occurs in the central region A, whereby both ends of the long cut line 21 can be broken and pushed open in the longitudinal direction (see FIG. 4B).

When both ends of the long cut line 21 are pushed open with the fingertip of the thumb H, the adjacent region B on both sides of the long cut line 21 can be cut along the virtual cutting line D (see FIG. 5B). In this case, the adjacent region B can be easily cut without impairing the outer appearance along the virtual cutting line D with the pair of first adjacent cut lines 24, 25 and the second adjacent cut line 22 arranged in the adjacent region B. In particular, since the second adjacent cut line 22 is arranged in the adjacent region B in addition to the pair of first adjacent cut lines 24, 25, the adjacent region B can be reliably cut even if the width dimension of the adjacent region B is widened according to the width dimension of the adhesive tape 1.

After the adjacent region B is completely cut, the cutting of the outer region C is advanced along the plurality of outer cut lines 23 (see FIG. 5C), and eventually, the adhesive tape 1 can be cut to the desired length (see FIG. 5D). The outer region C can also be easily cut without impairing the outer appearance by the outer cut lines 23 arrayed in a perforation form. Therefore, the adhesive tape 1 can be cut substantially linearly without impairing the outer appearance of the entire cut edge along the virtual cutting line D.

Figure 7:
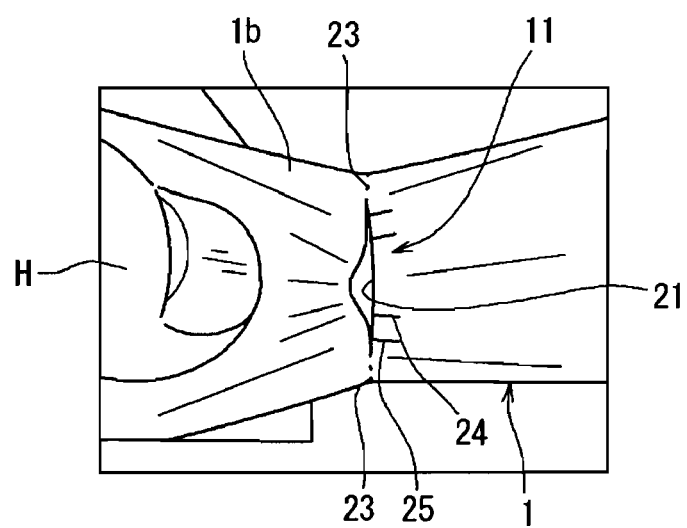
FIG. 7 is a plan view showing a state in which the thumb is pressed on the adhesive tape.

All of the shape of a distal end edge when the fingertip of the thumb H is seen from the upper side (see FIG. 5A-FIG. 5D), the shape along the longitudinal direction of the finger when the ball H1 of the fingertip is seen from the side (see FIG. 4A and FIG. 4B), and the shape along a finger width direction of the ball H1 of the fingertip are curved to a substantially arcuate shape, and thus when the fingertip is pressed on the adhesive tape 1, the adhesive tape 1 is concavely deformed to an arcuate shape along the width direction irrespective of the angle at which the fingertip is pressed on the adhesive tape 1 (see FIG. 7).

Thus, in the adjacent region B and the outer region C of the adhesive tape 1, a step is formed between a place closer to the center in the width direction and a place closer to the side edge 1b of the adhesive tape 1, respectively. The step causes a shearing stress to act in addition to the tensile stress on the cutting portion 11. Thus, the adjacent region B and the outer region C can also be cut without a problem along the virtual cutting line D.

As described above, according to the adhesive tape 1 of the present embodiment, when feeding out the adhesive tape 1, the tensile strength in the longitudinal direction is ensured by the regions of both sides including the adjacent region B and the outer region C, and thus the adhesive tape 1 can be fed out without being cut.

In cutting, the vicinity of the long cut line 21 that is opened is pressed with the finger to generate stress concentration and cut the adjacent region B. In this case, the first adjacent cut lines 24, 25 extending in the longitudinal direction are formed in the adjacent region B, and thus the adhesive tape 1 cannot be cut even if the adhesive tape 1 is pulled in the longitudinal direction but is easily cut by the stress concentration that occurs when pressed with the finger. Thus, the cutting sequentially advances in the outer region C, and the outer region C can be easily cut without impairing the outer appearance.

The outer cut line 23 of the outer region C may be set to a dimension of being relatively easily cut. At the time of cutting by the user described above, a greater stress acts on the outer region C in the virtual cutting line D by the long cut line 21 of the central region A where the stress concentration occurs, the central region A being closer to the finger of the operator than the side edge 1b side of the adhesive tape 1. Thus, the possibility of the cutting occurring with the side edge 1b side of the adhesive tape 1 as a starting point is low.

Further, the outer cut line 23 of the outer region C is provided to advance the cutting of the outer region C along the virtual cutting line D after the adjacent region B is cut. When the width dimension W of the adhesive tape 1 is wider than the width dimension of the finger of the operator and a sufficient stress is less likely to be exerted when the operator presses the adhesive tape 1 with the finger, the region where the stress is less likely to be exerted is set as the outer region C and the outer cut line 23 is provided.

Thus, in the adhesive tape 1 of the present embodiment, the adhesive tape 1 can be easily cut with a one-touch operation of pulling out the adhesive 1, and rotating the roll core 2 while holding down the adhesive tape 1 at the desired portion with the thumb H.

The operation of pressing the long cut line 21 portion of the adhesive tape 1 with the fingertip of the thumb H may be carried out other than through the method of pivoting the roll R1 by a constant angle, such as by pivoting the fed adhesive tape 1 by a constant angle toward the diagonally upper right side in FIG. 4A and FIG. 4B with the fingertip of the thumb H as the starting point, and gradually winding the adhesive tape 1 around the ball H1 of the fingertip with the hand gripping the adhesive tape 1.

In the embodiment described above, the cutting portions 11 are formed at a pitch interval of 10 mm along the longitudinal direction, and thus the operator can cut the adhesive tape 1 without a problem without particularly being conscious of the positions of the cutting portions 11.

Figure 6A:
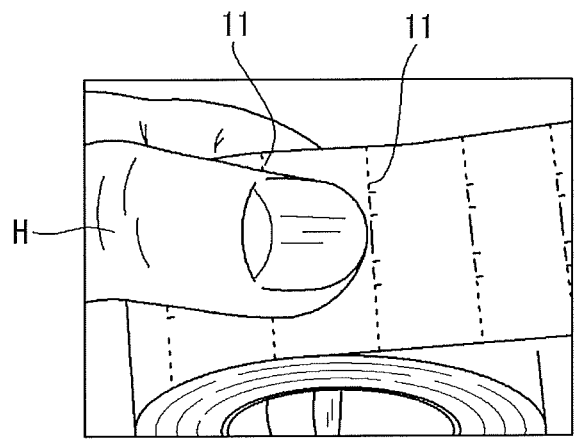
FIG. 6A is a perspective view showing which the fingertip of the thumb is pressed immediately close to the arbitrary cutting portion of the adhesive tape.

This aspect will be further described in detail with reference to FIG. 6A-FIG. 6C. FIG. 6A shows a case in which the fingertip of the thumb H is pressed immediately close to the arbitrary cutting portion 11 of the adhesive tape 1, FIG. 6B shows a case in which the fingertip is directly pressed on the cutting portion 11, and FIG. 6C shows a case in which the fingertip is pressed on substantially the central position of the cutting portion 11 and the cutting portion 11 adjacent thereto.

Figure 6B:
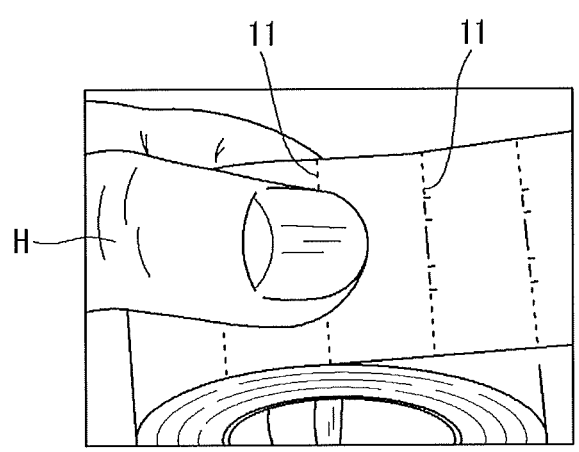
FIG. 6B is a perspective view showing a state in which the fingertip is directly pressed on the cutting portion.
Figure 6C:
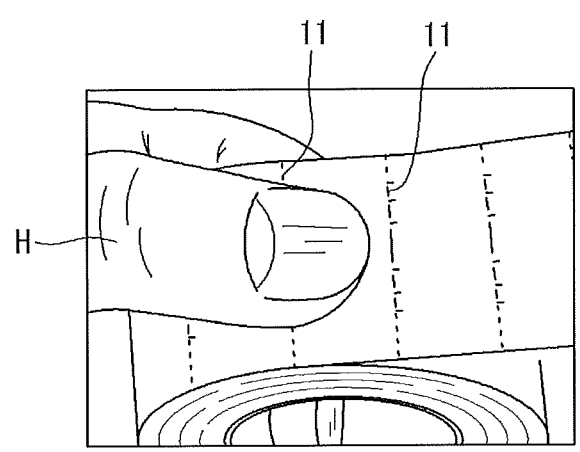
FIG. 6C is a perspective view showing state in which the fingertip is pressed on substantially the central position of the cutting portion and the cutting portion adjacent thereto.

As apparent from FIG. 6A-FIG. 6C, even if the fingertip is pressed on any position of the adhesive tape 1, the cutting portion 11 always exits in the vicinity (range of within 10 mm)

As described above, the adhesive tape 1, on which the fingertip is pressed, is concavely deformed to an arcuate shape along the width direction, and thus vicinity of the center in the width direction of the long cut line 21 is most strongly pulled. Therefore, even if the fingertip pressed on the adhesive tape 1 is spaced away from the cutting portion 11 in the vicinity thereof, both ends of the long cut line 21 can be broken without a problem.

In this case as well, the adhesive tape 1 is concavely deformed to an arcuate shape along the width direction, so that a step is formed between a place closer to the center in the width direction and a place closer to the side edge 1b of the adhesive tape 1 in the adjacent region B and the outer region C of the adhesive tape 1. The step causes the tensile stress and the shearing stress to act on the cutting portion 11. Thus, the adjacent region B and the outer region C can also be cut without a problem along the virtual cutting line D.

Therefore, the operator can cut the adhesive tape 1 without a problem by the cutting portion 11 in the vicinity of the position where the operator desires to cut without particularly being conscious of the existence of the cut line 20. Thus, the operation of cutting the adhesive tape 1 can be efficiently carried out.

Therefore, according to the roll tape R of the present embodiment, the central region A includes the long cut line 21 that opens by feeding the adhesive tape 1 and that enables the adhesive tape 1 to be cut along the virtual cutting line D with both ends of the central region A as the starting points by pressing the central region A or the vicinity thereof with the finger in such opened state, so that the adhesive tape 1 can be cut substantially linearly without impairing the outer appearance of the entire cut edge along the virtual cutting line D.

Figure 8:
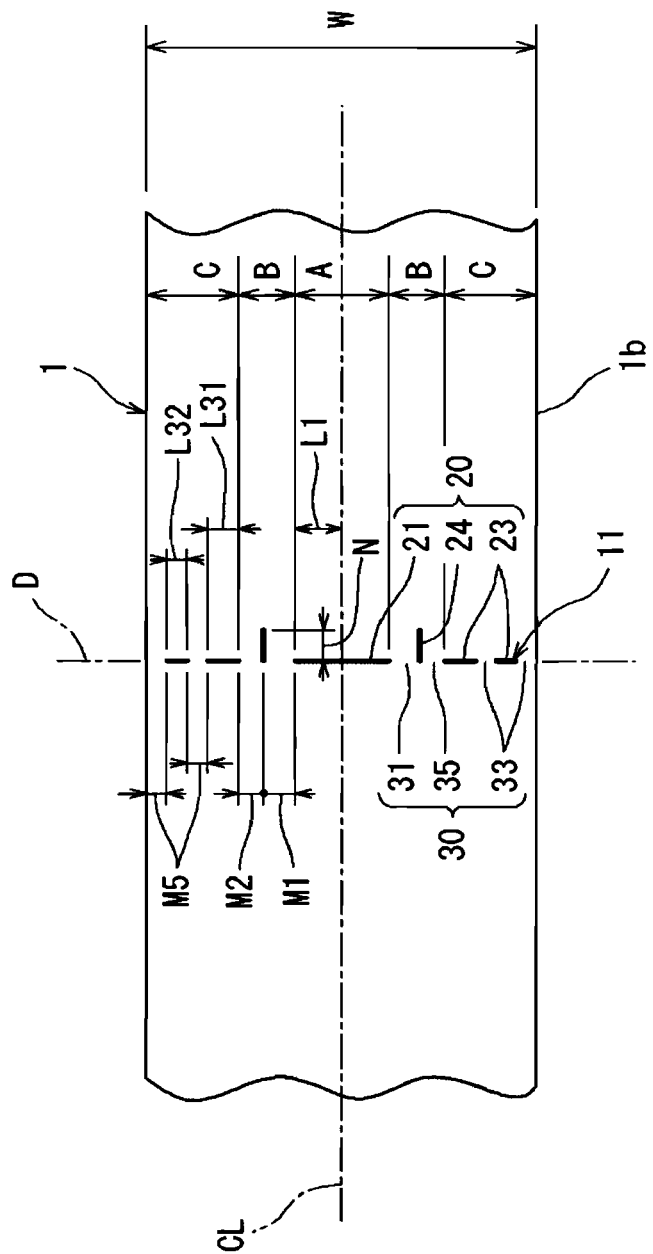
FIG. 8 is a partially enlarged view showing a cutting portion of a roll tape according to a second embodiment of the present invention.

FIG. 8 is a partially enlarged view showing the cutting portion 11 of the roll tape R according to a second embodiment of the present invention. The present embodiment differs from the first embodiment in that the width direction dimension W of the adhesive tape 1 is set to 12.5 mm, the first adjacent cut line 25, which is one of the pair of first adjacent cut lines, is not formed, and the uncut portions 32, 34 are not formed.

The cut line 20 configuring the cutting portion 11 of the second embodiment includes the long cut line 21 arranged in the central region A, the first adjacent cut line 24 arranged in the adjacent region B by way of the uncut portion 31, and a plurality of outer cut lines 23 arranged in the outer region C by way of the uncut portion 35.

The width direction dimension L1, L31, L32 of each of the cut line portions, the width direction dimension M1, M2, M5 of each uncut portion, and the longitudinal direction dimension N of the first adjacent cut line 24 are set as below.

W=12.5 mm
L1=1.5 mm
L31=1 mm
L32=0.65 mm
M1=1 mm
M2=0.8 mm
M5=0.65 mm
N=1 mm

Figure 9A:
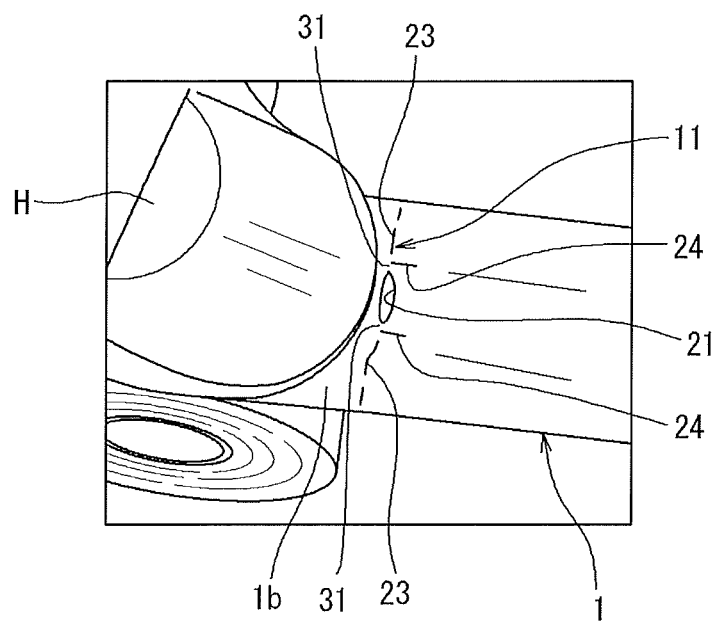
FIG. 9A is a perspective view showing a state in which the long cut line is pressed by the fingertip of the thumb.
Figure 9B:
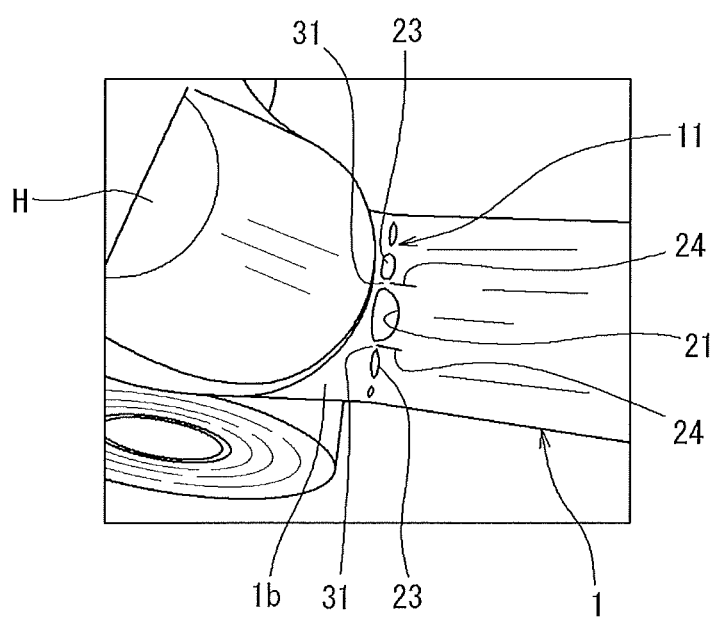
FIG. 9B is a perspective view of an adhesive tape pressed more strongly than the adhesive tape illustrated in FIG. 9A.

In the second embodiment, the fingertip is merely pressed on the opened central cut line 21 portion, similar to the first embodiment, to cut the adhesive tape 1 (see FIG. 9A and FIG. 9B).

In the adhesive tape 1 of the present embodiment, the width direction dimension W is set to 12.5 mm, which is a value the same as or slightly smaller than the width dimension of the thumb H of the adult. Thus substantially the entire region in the width direction of the adhesive tape 1 can be pressed when the surface of the adhesive tape 1 is pressed with the thumb H. In such a case, the adhesive tape 1 can be easily pushed through even if the width direction dimension of the uncut portion 30 is set slightly large.

Thus, in the present embodiment, the adhesive tape 1 can be easily pushed through even if only one first adjacent cut line 24 extending in the longitudinal direction is arranged in each adjacent region B.

Therefore, the first adjacent cut line 24 extending in the longitudinal direction in the cut portion 11 can be arranged with the preparing number appropriately adjusted according to the adhesive tape 1.

In the cut line 20 of the present embodiment, only one first adjacent cut line 24 is arranged, and thus the dimension of the uncut portion 33 positioned between the adjacent outer cut lines 23 is set greater than that in the case of the first embodiment (0.59 mm) so that the tensile strength of the cut line 20 is adjusted to become appropriate.

Thus, the dimension of each uncut portion 30 can be appropriately adjusted and set according to the width direction dimension W, and the like of the adhesive tape 1.

Figure 10:
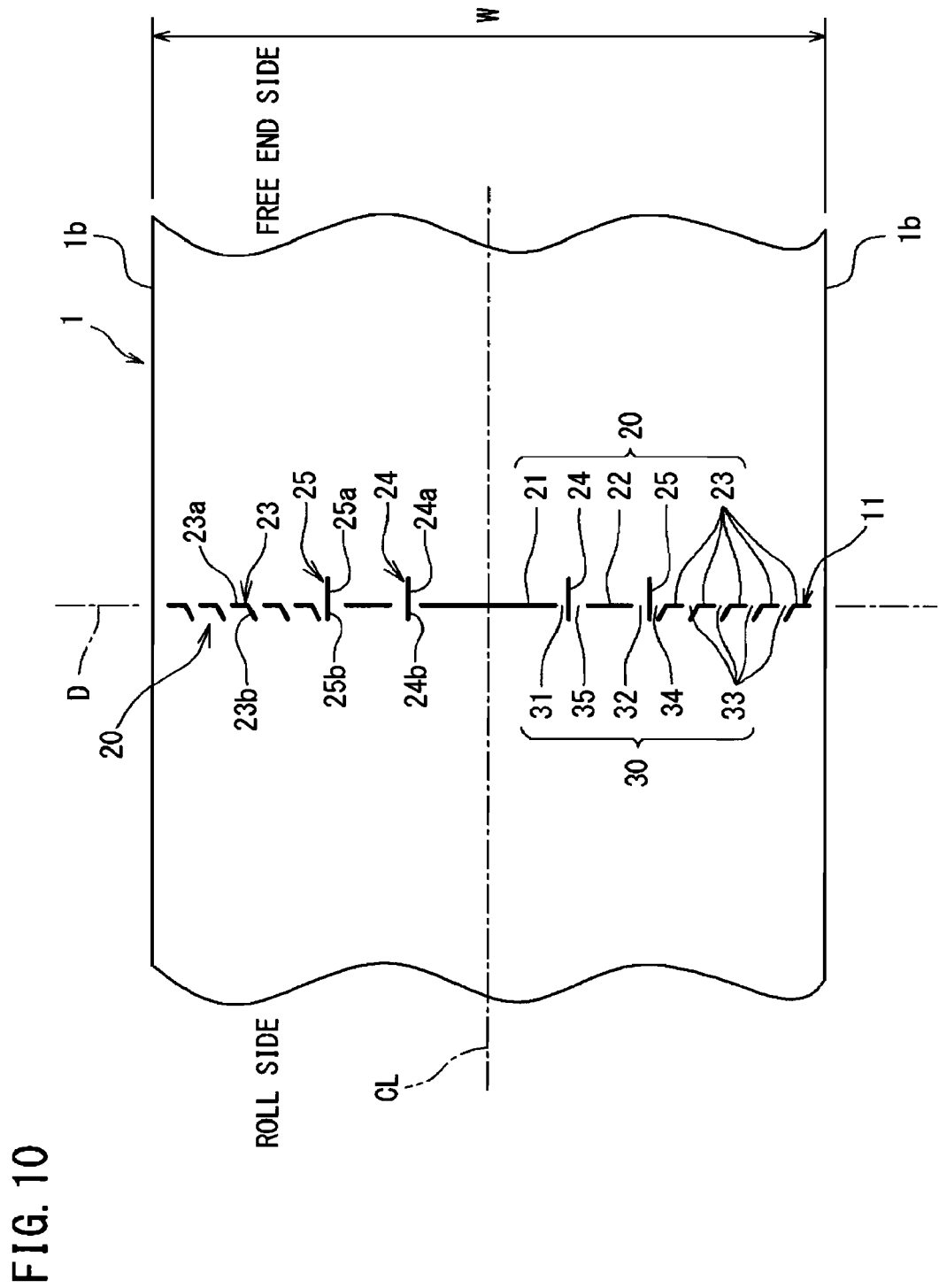
FIG. 10 is a partially enlarged view showing a cutting portion of an adhesive according to a third embodiment of the present invention.

FIG. 10 is a partially enlarged view showing the cutting portion 11 of the adhesive tape 1 according to a third embodiment of the present invention. The present embodiment differs from the first embodiment in that the first adjacent cut lines 24, 25 are arranged to intersect with the virtual cutting line D, and the outer cut line 23 includes a slanted portion 23b extended in an inclined manner with respect to the width direction.

The first adjacent cut lines 24, 25 are extended in the longitudinal direction of the adhesive tape 1, and are arranged to intersect with the virtual cutting line D. The first adjacent cut lines 24, 25 of the present embodiment are configured by first portions 24a, 25a, which are on the free end side of the adhesive tape 1 than the virtual cutting line D, and second portions 24b, 25b, which are on the roll R1 (FIG. 1) side than the virtual cutting line D, respectively.

The second portions 24b, 25b are set to have a dimension shorter than the first portions 24a, 25a.

Each of outer cut lines 23 of the present embodiment is configured by a width direction portion 23a formed along the virtual cutting line D (along the width direction), and the slanted portion 23b extending in the diagonal direction with an end on the center line CL side of the width direction portion 23a as a base end.

The slanted portion 23b is extended in the diagonal direction so as to gradually approach the center line CL from the end of the width direction portion 23a toward the roll R1 side in the longitudinal direction of the adhesive tape 1.

The distal end of the slanted portion 23b and the distal ends of the second portions 24b, 25b of the first adjacent cut lines 24, 25 are formed to be at substantially the same position in the longitudinal direction of the adhesive tape 1.

Figure 11:
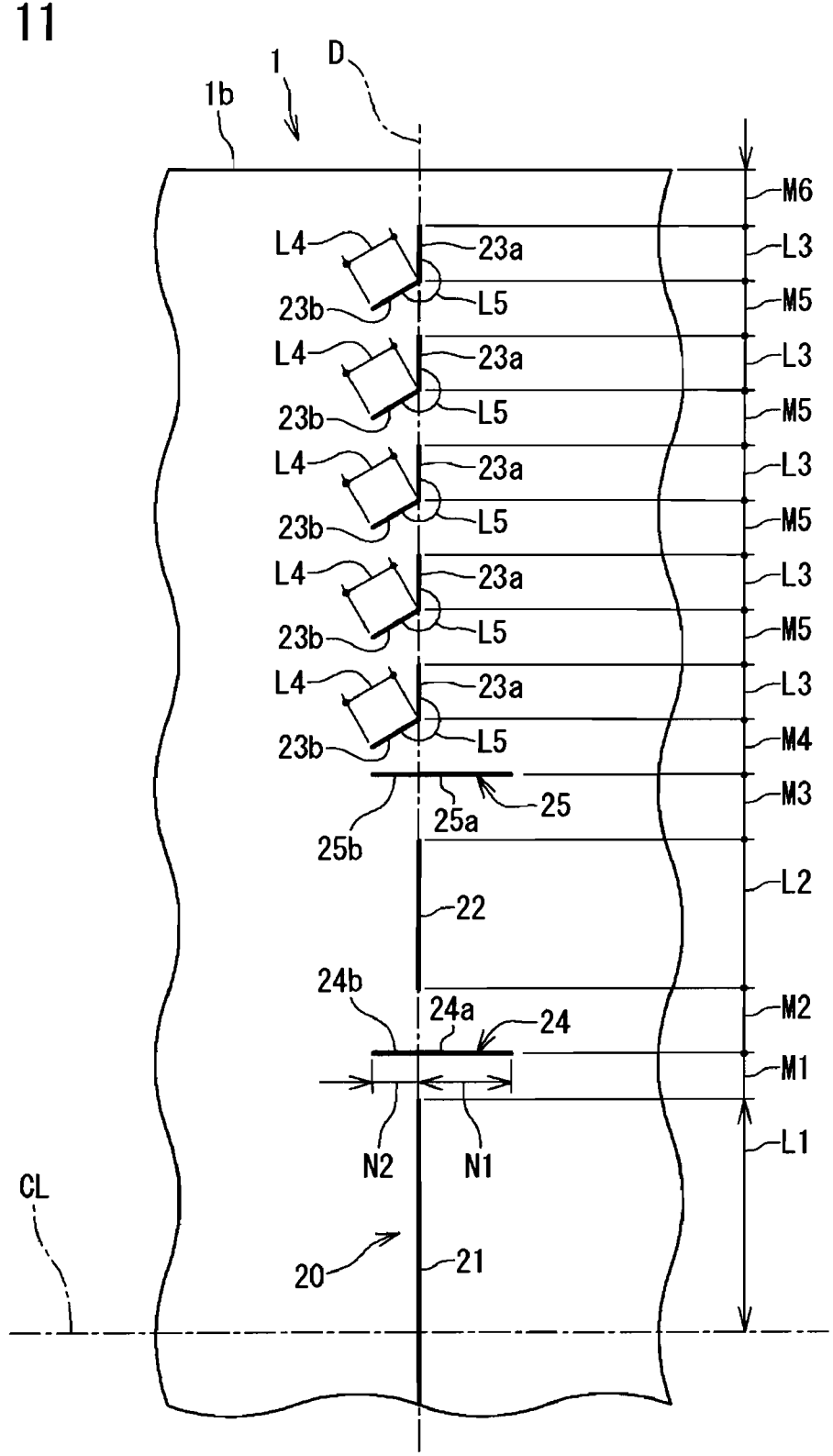
FIG. 11 is an enlarged view of the main parts of FIG. 10.

FIG. 11 is an enlarged view of the main parts of FIG. 10.

In the present embodiment, the width direction dimension W of the adhesive tape 1 is 25 mm, and the width direction dimensions L1 to L3 of each of the cut lines 20, the dimension L4 of the slanted portion 23b, the angle L5 of the slanted portion 23b with respect to the width direction portion 23a, the width direction dimensions M1 to M6 of each uncut portion 30, and the longitudinal direction dimensions N1, N2 of the first and second portions 24a, 24b, 25a, 25b in the first adjacent cut lines 24, 25 are set as below.

L1=2.5 mm
L2=1.6 mm
L3=0.59 mm
L4=0.59 mm
L5=240 degrees
M1=0.5 mm
M2=0.7 mm
M3=0.7 mm
M4=0.59 mm
M5=0.59 mm
M6=0.6 mm
N1=1.0 mm
N2=0.5 mm According to the adhesive tape 1 of the present embodiment, a number of the cut lines extending toward the roll R1 side than the virtual cutting line D are arranged, and hence the cut edge when the adhesive tape 1 is cut is cut more accurately along the virtual cutting line D, and the appearance of the cut edge can be effectively suppressed from being impaired.

In particular, since each of the outer cut lines 23 includes the slanted portion 23b, the outer appearance of the cut edge when the outer region C is cut can be effectively suppressed from being impaired while the tensile stress in the region (region corresponding to the outer region C shown in FIG. 2) formed with the outer cut line 23 is maintained to an appropriate degree.

Figure 12:
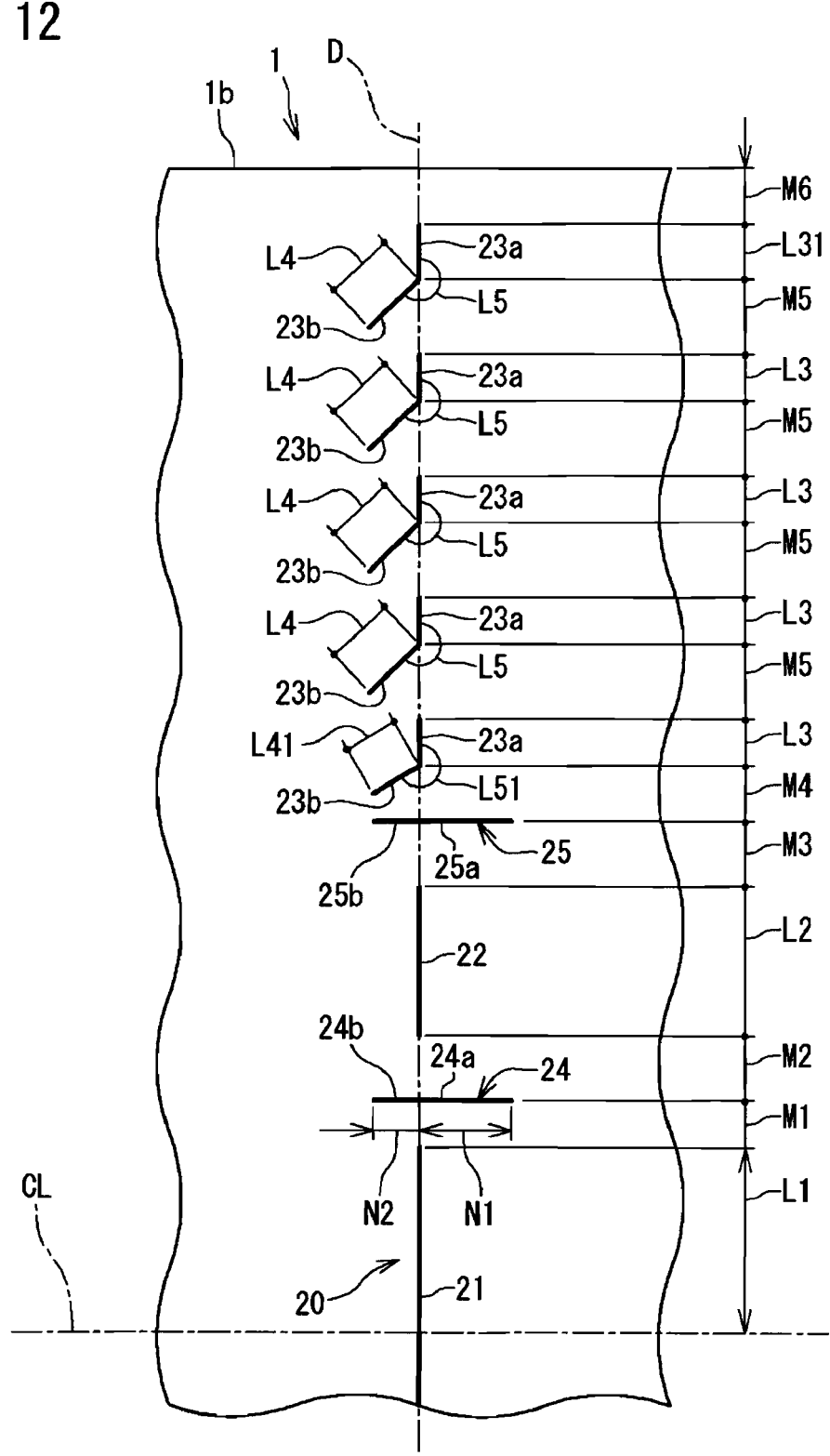
FIG. 12 is a partially enlarged view of an adhesive tape according to a first variant of the third embodiment, and shows a cutting portion in an enlarged manner.

FIG. 12 is a partially enlarged view of the adhesive tape 1 according to a first variant of a third embodiment, and shows the cutting portion 11 in an enlarged manner. The cutting portion 11 of the present variant has the dimensions of each outer cut line 23 and each of the uncut portions 33 positioned between the outer cut lines 23 is adjusted so that the tensile load leading to cutting becomes greater than the cutting portion 11 of the adhesive tape of the first variant.

The "tensile load leading to cutting" described herein does not indicate a case of actively cutting with hand, but indicates, for example, the load leading to the cutting of the adhesive tape 1 when the tensile stress in the longitudinal direction is acted on the adhesive tape 1 by, for example, attaching a weight, and the like on an adhesive material 1a stacked on the back surface of the adhesive tape 1 and suspending the weight with the adhesive tape 1.

The cutting portion 11 of the adhesive tape 1 of the third embodiment shown in FIG. 10 and FIG. 11 can withstand the tensile load of 500 g, for example, but if the tensile load with which the adhesive tape 1 without the cutting portion 11 leads to cutting is significantly greater than 500 g, the tensile strength of the adhesive tape 1 may be greatly lowered by the arrangement of the cutting portion 11.

With regards to this, in FIG. 12 showing the present example, the proportion of the dimension of each uncut portion 30 and the dimension of each of the cut lines 20 is adjusted to obtain a strength that can sufficiently withstand the tensile load of 750 g, where the tensile strength is further increased and the tensile load leading to cutting is increased than as shown in FIG. 10 and FIG. 11.

In the first variant of the third embodiment, the width direction dimension W of the adhesive tape 1 is 25 mm, and the width direction dimension L1 to L3, L31 of each of the cut lines 20, the dimension L4, L41 of the slanted portion 23b, the angles L5, L51 of the slanted portion 23b with respect to the width direction portion 23a, the width direction dimensions M1 to M6 of each uncut portion 30, and the longitudinal direction dimensions N1, N2 of the first and second portions 24a, 24b, 25a, 25b in the first adjacent cut lines 24, 25 are set as below.

L1=2.0 mm
L2=1.6 mm
L3=0.5 mm
L31=0.59 mm
L4=0.75 mm
L41=0.59 mm
L5=227 degrees
L51=240 degrees
M1=0.5 mm
M2=0.7 mm
M3=0.7 mm
M4=0.59 mm
M5=0.805 mm
M6=0.6 mm
N1=1.0 mm
N2=0.5 mm According to FIG. 12 showing the present example, the proportion of the dimension of each uncut portion 30 with respect to the dimension of each of the cut lines 20 is adjusted so as to become greater than the adhesive tape 1 of the third embodiment shown in FIG. 10 and FIG. 11, thus increasing the tensile load leading to the cutting. As a result, the tensile strength of the adhesive tape 1 can be suppressed from being greatly lowered.

Figure 13:
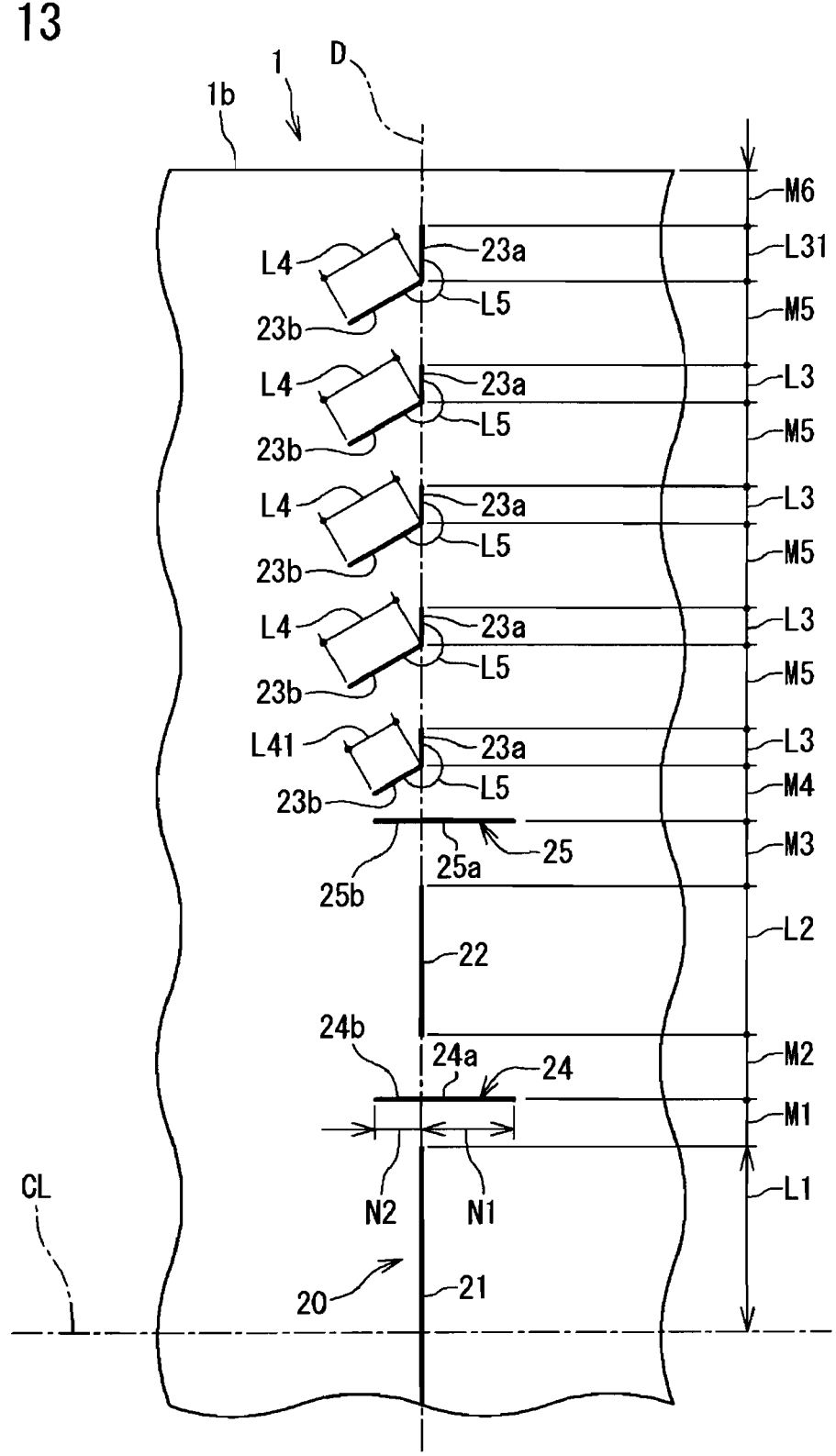
FIG. 13 is a partially enlarged view of an adhesive tape according to a second variant of the third embodiment, and shows a cutting portion in an enlarged manner.
Figure 14A:
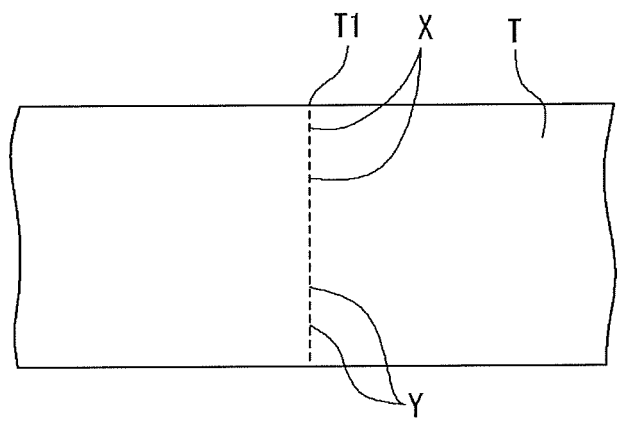
FIG. 14A is a schematic plan view showing an adhesive tape in which a cut line is arranged in a perforation form.
Figure 14B:
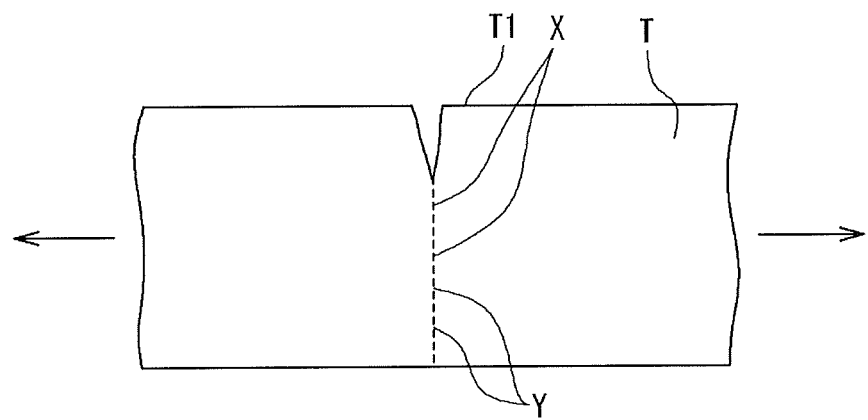
FIG. 14B is a schematic plan view showing a state in which the adhesive tape shown in the FIG. 14B is cut.
Figure 15A:
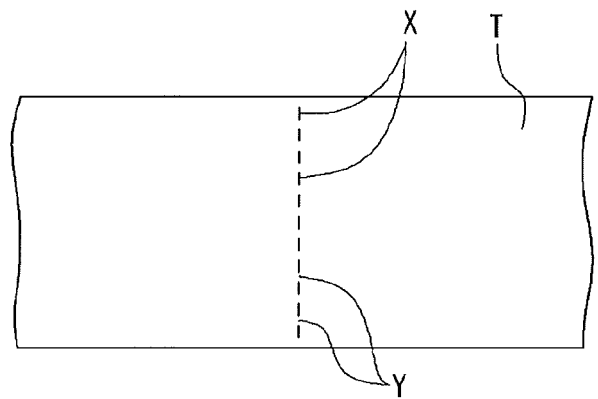
FIG. 15A is a schematic plan view showing an adhesive tape in which another cut line in a perforation form is arranged.
Figure 15B:
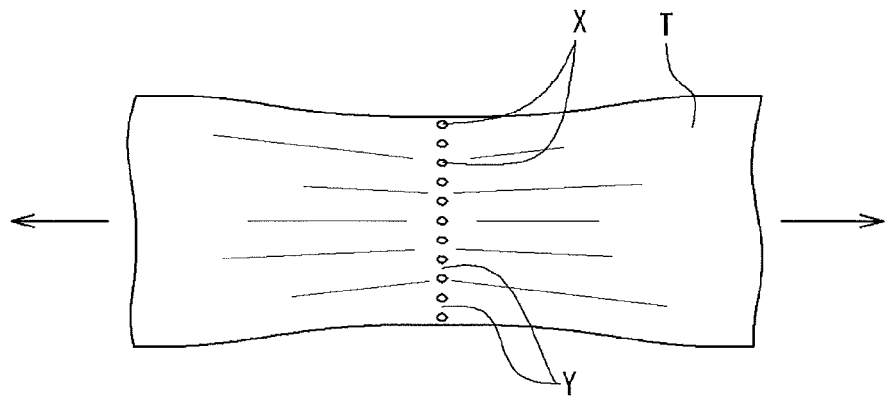
FIG. 15B is a schematic plan view showing a state in which the adhesive tape shown in the FIG. 15B is pulled.

FIG. 13 is a partially enlarged view of the adhesive tape 1 according to a second variant of the third embodiment, and shows the cutting portion 11 in an enlarged manner. In the cutting portion 11 of the present variant as well, the dimension of each outer cut line 23 and each uncut portion 33 positioned between the outer cut lines 23 is adjusted, so that the tensile load leading to cutting is made greater than that in the cutting portion 11 of the third embodiment and the first variant.

In the second variant of the third embodiment, the width direction dimension W of the adhesive tape 1 is 25 mm, and the width direction dimension L1 to L3, L31 of each of the cut lines 20, the dimensions L4, L41 of the slanted portion 23b, the angle L5 of the slanted portion 23b with respect to the width direction portion 23a, the width direction dimension M1 to M6 of each uncut portion 30, and the longitudinal direction dimensions N1, N2 of the first and second portions 24a, 24b, 25a, 25b in the first adjacent cut lines 24, 25 are set as below.

L1=2.0 mm
L2=1.6 mm
L3=0.4 mm
L31=0.59 mm
L4=0.9 mm
L41=0.59 mm
L5=240 degrees
M1=0.5 mm
M2=0.7 mm
M3=0.7 mm
M4=0.59 mm
M5=0.905 mm
M6=0.6 mm
N1=1.0 mm
N2=0.5 mm In FIG. 13 showing the present example as well, the proportion of the dimension of each of the uncut portions 30 with respect to the dimension of each of the cut lines 20 is adjusted to obtain a strength that can sufficiently withstand the tensile load of 1000 g, and the tensile load leading to the cutting can be further increased than in the cutting portion 11 of the third embodiment and the first variant.

Thus, the adhesive tape 1 of the present embodiment can adjust the tensile load leading to the cutting in the cutting portion 11, and hence can be adjusted to an appropriate tensile load according to the tensile load of the adhesive tape 1 itself.

The present invention is not limited to the embodiments described above. In each embodiment, a case in which the first adjacent cut lines 24, 25 are formed in the cutting portion 11 is shown, but for example, if the width direction dimension of the adjacent region B is set relatively narrow in a range that a predetermined tensile strength can be ensured, the first adjacent cut lines 24, 25 may not be arranged and only the second adjacent cut line 22 may be arranged in the cutting portion 11. This is because if the adjacent region B is set relatively narrow, the adjacent region B can be cut relatively easily with only the second adjacent cut line 22 even if the first adjacent cut lines 24, 25 are not arranged.

If the width dimension W of the adhesive tape 1 is extremely narrower than the width of the finger of the adult, for example, and the outer region C cannot be ensured, the outer cut line 23 may not be formed.

In each embodiment described above, a case of applying to the surgical tape has been described for the adhesive tape of the present invention, but for example, application can be made on the adhesive tape formed using a material having an appropriate strength and flexibility such as vinyl adhesive tape, and the like.

REFERENCE SIGNS LIST

1: adhesive tape
1a: adhesive
1b: side edge
1c: tape main body
2: roll core
11: cutting portion
20: cut line
21: long cut line
22: second adjacent cut line
23: outer cut line
24: first adjacent cut line
25: first adjacent cut line
30: uncut portion
A: central region
B: adjacent region
C: outer region
D: virtual cutting line

The invention claimed is:

1. A adhesive tape roll, comprising:
an elongate substrate with a plurality of cut lines, each formed along a virtual cut line extending in a width direction of the adhesive tape, the cut lines being arranged to cut the adhesive tape to a desired length while being fed out with a predetermined length; and
an adhesive provided on one surface of the elongated substrate,
wherein each of the cut lines includes:
a long cut line segment, which is arranged in a central region in the width direction of the virtual cut line and is opened by feeding out the adhesive tape, and
a both-side cut line segment formed of a plurality of cuts and arranged in regions on both sides of the central region in the width direction of the central region, the cuts of the both-side cut line segment being shorter than the long cut line segment,
wherein the long cut line segment is adapted to cut the adhesive tape along the both-side cut line segment with both ends of the central region as starting points, by pressing the central region or a vicinity of the central region with a finger in the opened state,
the regions on both sides have a tensile strength that withstands a tensile stress generated when the adhesive tape is fed out, and
the both-side cut line segment includes a first adjacent cut line arranged in an adjacent region adjacent on both sides of the central region of the regions on both sides, and the first adjacent cut line extends in a longitudinal direction of the adhesive tape while intersecting the virtual cut line.

2. The adhesive tape roll according to claim 1, wherein the both-side cut line segment includes a plurality of perforations outward from the first adjacent cut line in the width direction of the adhesive tape.

3. The adhesive tape roll according to claim 1, wherein a second adjacent cut line extending along the virtual cut line is arranged adjacent to the first adjacent cut line in the adjacent region.

4. The adhesive tape roll according to claim 1, wherein the elongated substrate is made from a nonwoven cloth.

5. The adhesive tape roll according to claim 1, wherein the first adjacent cut line is adjacent to one end of the long cut line segment such that a first uncut portion is formed between the one end of the long cut line segment and the first adjacent cut line, and a second uncut portion is formed on a side of the first adjacent cut line opposite the long cut line segment.

* * * * *